United States Patent [19]

Tamm

[11] 4,006,988

[45] Feb. 8, 1977

[54] PHOTO-ELECTRIC DEPTH OR TURBIDITY METER FOR FLUID SUSPENSIONS

[76] Inventor: Per-Henric Sebastian Tamm, Lilljeborgsvagen 12, S-752 36 Uppsala, Sweden

[22] Filed: Mar. 26, 1975

[21] Appl. No.: 562,183

[52] U.S. Cl. .................................. 356/4; 250/574; 250/577; 356/208; 356/1
[51] Int. Cl.[2] .................. G01C 3/08; G01N 21/26
[58] Field of Search .......... 356/1, 4, 208; 250/574, 250/577

[56] References Cited

UNITED STATES PATENTS

| | | | |
|---|---|---|---|
| 2,324,304 | 7/1943 | Katzman | 356/208 |
| 3,170,151 | 2/1965 | Roth | 356/1 |
| 3,317,730 | 5/1967 | Hilsum | 250/574 |
| 3,412,253 | 11/1968 | Marcus | 250/574 |
| 3,549,893 | 12/1970 | Gibbs | 250/577 |
| 3,608,723 | 9/1971 | Brown | 250/574 |

Primary Examiner—Maynard R. Wilbur
Assistant Examiner—S. C. Buczinski
Attorney, Agent, or Firm—Cushman, Darby & Cushman

[57] ABSTRACT

An instrument functioning as either a turbidimeter or as a depth meter for measuring the distance from the instrument to the level of a turbid fluid. A light source provided with an optical system emits a beam of light to the fluid, and the volume or "beam of vision" viewed by a photo-cell likewise provided with an optical system intersects said beam of light. The two beams include a relatively small angle so that a tapered or conical volume of intersection in the fluid is obtained. Thus, the quantity of light scattered or reflected within this volume and reaching the photo-cell is dependent on the turbidity and the position of this level. The light emitted by the light source is modulated at a relatively high frequency. The output of the photo-cell passes through a frequency filter and is, then, indicated or recorded as a measure of turbidity or of depth of said layer.

6 Claims, 1 Drawing Figure

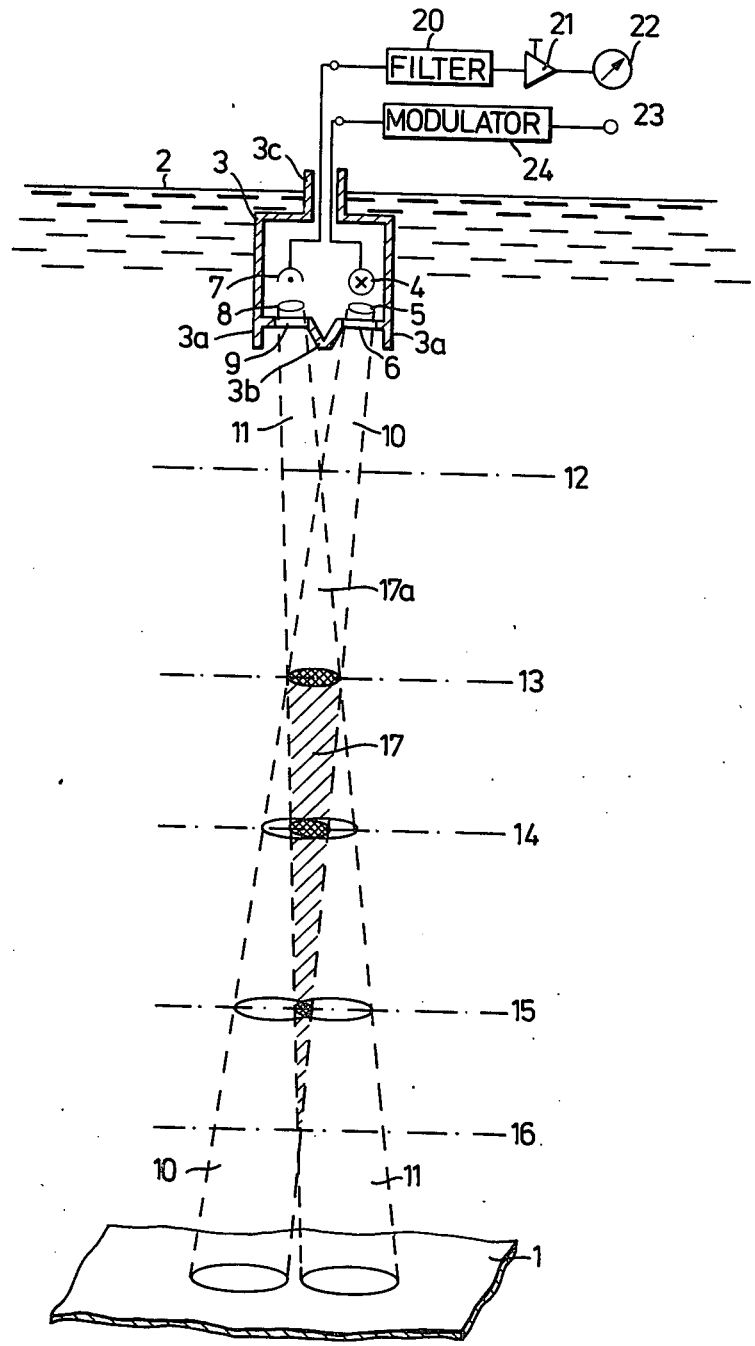

PHOTO-ELECTRIC DEPTH OR TURBIDITY METER FOR FLUID SUSPENSIONS

The invention relates to a photo-electric level or turbidity meter for measuring the upper level of a turbid fluid layer, especially in a stratified fluid, or the turbidity of the fluid by transmitting a beam of light from a light source provided with an optical system into the fluid and by measuring the light, scattered or reflected by the particles making the fluid turbid, with photo-cell means.

It is known that the turbidity of a fluid or the depth of a turbid layer in a fluid can be determined by an illuminating device and a photo-electric cell to measure the light permeability, i.e. the transmission of the fluid, and to indicate the measured turbidity or level of a turbid layer. It is also known that light reflected by particles in the fluid (scatter measurement, nephelometry) can be measured as in, for example, the determination of cloud altitude, fog (transparency of the atmosphere and range of sight) and concentration of smoke and that this method can also be applied in hydrology an and chemical analysis.

The above measuring methods play an important role in several different fields. For example, it is often required to determine the particle content of air, gas, fuel gas, steam and liquids such as beer, wines, soft drinks, solvents, fuels, surface treatment fluids, photographic fluids, chemical substances in liquid form, as well as particles in water. The particles may be solid, amorphous or crystalline or may consist of organic cells or other complicated bodies. The particles can also be gas bubbles or undissolved drops of liquid in a fluid or an emulsion. It is often desired to measure, for example, aqueous suspensions or dispersions of cellulose fibres or other suspended material in sediment basins in determining the degree of turbidity and/or the level of the suspension layer below the level of the surface of the water. Similar measurements are made with apparatus designed to warn of sludge escape in sedimentation plants, tp supervise the re-generation of filter beds, to control sludge pumps in sludge thickening vessels and the like, or to indicate the mass of suspended material per unit volume liquid etc. In all of these cases, when it situ measurement is required, it is desirable or even required that the measuring device or at least the aperture for the beam of light and the optical aperture (window) of the photo-cell are submerged in the liquid. For this reason, an ordinary transmission measurement has the serious disadvantage that the measured value is dependent not only on the turbidity of the liquid but also on the substances dissolved in it, in particular colouring substances and other substances impeding transmission of light. Besides, the effective transmission of the above-mentioned apertures, which are covered with glass or other transparent material, varies because of deposits, especially those of the suspended material, but also of organic growth or chemical precipitation. Even known reflection measurement involves similar and other difficulties. The above-mentioned difficulties are considerably reduced or even eliminated altogether, as the case may be, by the invention defined in the main claim.

The accompanying drawing diagrammatically shows an example of a measuring device designed in accordance with the invention.

Above a bottom 1 in a container, pipe, drum, channel or the like, a fluid is either standing still or flowing, and is assumed to be mainly water with an upper surface 2. A water-tight measuring head 3 is submerged in the water and contains an electric light source 4 of the type in which the light is electrically controllable, preferably a luminescent diode. The lamp 4 is associated with a suitable optical system 5 and a window 6 in the measuring head 3 to emit a beam 10 of light. The measuring head also contains a photo-cell 7 associated with a suitable optical system or lens 8 and another window 9 in the measuring head. The said beam of light 10 and the beam 11 of vision of the photo-cell 7 are shown as slightly divergent, their optical axes including a small angle and being directed downwards and intersect each other. The photo-cell can be a passive or an active photo-cell e.g. a photo-diode, photo-transistor, photo-resistor or the like.

At the bottom of the measuring head 3 there is arranged a shielding collar 3a which reduces the risk of fouling windows 6 and 9 and improves the possibility of flushing these windows, if required, with a cleaning liquid mentioned more below. Between the windows 6 and 9 of the measuring head an optical screen 3b projects and prevents scattered light occurring in the vicinity of the window 6 from reaching the window 9 of the photo-cell. Such optical shielding in one form or another is important. The measuring head is also fitted with a water-tight cable inlet at 3c and, if desired, also with a means of attachment at the same point. The inlet is shown, it is true, partially above the surface of the water 2 but, in practice, is nearly always situated below the surface of the water. Naturally, the light source 4 and the photo-cell 7 must be optically screened from each other even inside the measuring head although this screening is not illustrated.

In view of light scattering in the water and especially in a turbid layer of the same, the drawing and the description are somewhat idealised in order to simplify the presentation.

The light and vision beams 10 and 11 intersect each other within the region between levels 12 and 16. The level measuring area lies between levels 13 and 16, the level 13 preferably being that level at which the common intersection area the two beams 10 and 11, the cross-hatched area in the drawing, is greatest. The volume 17 common to the two beams below level 13 is hatched in the drawing and forms the intersection region or volume used in measuring.

To light source 4 is fed from a current source 23, preferably a direct current from a battery for example. The current and, thus, also the light of the light source, are modulated by a modulator with a suitably chosen frequency in the range of 1–20 kHz. Alternatively, the source 23 and the modulator 24 may be replaced by a generator (oscillator) supplying the light source with alternating current of the said chosen frequency.

The photo-cell 7 is connected via a band-pass filter 20 to an amplifier 21 with manual and possibly also automatic setting of the amplification. The filter 20 allows only the chosen frequency to pass, and perhaps also higher and slightly lower frequencies. The filter may be a selective filter for just the modulation frequency, but preferably a band-pass filter or a high-pass filter, may be used because light of higher frequency does not normally occur in interfering external light.

If a layer of sludge or any other turbid layer such as a dispersion above the bottom 1 has an upper level at 13, a full reading on a measuring instrument connected to the amplifier output (ammeter or voltmeter) is obtained. If, for example, the level of the sludge layer lies more below, say at 14 a smaller reading is apparently obtained whilst the crosshatched intersection area at level 14 and therefore also the quantity of light reflected from this level is smaller than at 13. Still smaller readings are obtained at a sludge layer level 15 and, theoretically, no reading is obtained at level 16 or below. On account of light scattering and secondary reflection a weak photo-cell signal is in fact nevertheless obtained even from a level below 15 but this can be calibrated out by, for example, zero adjusting the instrument 22 and/or threshold adjustment of the amplifier 21 when measuring the required fluid zero level. If the sludge level rises above level 31, that is if such a case is not foreseen or is without interest in the level measuring, the common intersection area of the beams 10 and 11 naturally decreases again, but, in practice, the quantity of light reflected to the photo-cell probably does not decrease because the total optical losses in this area in relative proximity to the measuring head diminish sharply so that the photo-cell 7 receives much light even if the sludge level rises over and above the level 12 to the region where no common intersection area between the two beams exists but a sufficiently strong secondary reflection and light scattering from the light beam 10 to sight beam 11. In the area close to the measuring head 3 this scattering is perceptible even in clean water and is the reason why some sort of optical screen such as that at 3b really ought to be arranged between the two windows 6 and 9 although electrical compensation for this scattered would also be possible. This screen may form part of the collar or collars 3a, if preferred.

In the drawing, the criss-crossed common intersection area of the beams 10 and 11, e.g. at 13, does not in practice form a reflecting surface but a reflecting volume having a non-negligible depth within the intersection area 17, and this depth depends on the turbidity and the reflecting or scattering properties of the clouding particles. Since a certain given level meter is normally to be used only for one single purpose, i.e. since one does not usually use one and the same level meter one time for sludge layers in a sewerage purification plant or decanting plant and another time for measuring fibre suspension layers in the pulp industry, the dependence of the level measurement on the qualities of the turbidity is also basically a question of calibration. If, for example, the level of the sludge layer is at 13, the amount of reflected and scattered light from particles below this level and received by the photo-cell probably decreases exponentially with the vertical distance from 13 and to this is added that the area of the illuminated volume 17 of intersection also decreases downwards so that the reflection from the depth will be even less pronounced. For this and other reasons, even a change in the degree of turbidity of the sludge layer is in practice of little importance to the measuring accuracy, and the measuring error can in general be kept within a few percent.

Measuring accuracy and the possibility of measuring slight changes in level increase if the angle between the optical axes of the two beams 10 and 11 is widened (upper limit approx. 178°), but the level measuring area corresponding to the level area between 13 and 16 is considerably decreased, and for reasons referred to below, the angle should or even must be small.

If each of the beams 10 and 11 itself forms a divergent beam the level measuring area can apparently be increased by increasing the divergence of one or both beams but the measuring accuracy will be less unless other steps are taken such as increasing the angle between the two beams. Increasing the divergence angle also leads to greater light scattering away from the beams and light source 4 must be made stronger in otherwise the same conditions. Each individual beam 10 and 11 can also be a so-called parallel or cylindrical beam (divergence angle = zero) or a convergent beam. With convergence, the increase of the light losses with distance from the measuring head will be less perceptible, which might be desirable in certain cases but the level measuring area will decrease with increasing convergence.

As a practical example it may be mentioned that a suitable angle between the optical axes of the two beams (if the beams have approximately circular cross-section) is about 5° and that the divergence angle of any individual beam can be about the same if, for example, the level of a cellulose fibre suspension layer under water is to be measured. Generally suitable values of the angle between the axes of the two beams lie approximately between 3 and 25° and for the "divergence angle" of the individual beams approximately between −3 and +10° in dependence on the practical field application or field of use, operating conditions and the required level measuring area and measuring accuracy. Generally, the latter divergence angle should not exceed the range from −10 to +15°. If the level meter is used only to give a signal when one given single level (preferably adjacent to level 13) is exceeded by the sludge layer, the angle between the axes of the beams 10 and 11 ought to be made relatively large, and the individual beams should then, have a small, zero or negative divergence angle (negative divergence is convergence).

Thanks to the fact that no photo-cell signal is obtained at a sludge layer level below point 16, the level meter can be used even in confined or irregular spaces where side walls or solid objects could otherwise produce a signal.

The cross-section area of the beams 10 and 11 need not, of course, be circular but can have another e.g. elliptical or rectangular shape. Flat, band-shaped beams may be used such that the broad side of the flat beam extends in the plane of the drawing. Nor need the cross-sectional areas of the beams necessarily have identical forms or sizes. The measuring instrument 22 can be supplemented with or replaced by a trace recorder or other registering device e.g. a tape recorder or a strip puncher or a digital display, a feeding apparatus for computers, electronic or electro-magnetic relay devices for controlling a magnetic valve or a sludge pump, or similar measurement indicator for telemetry or control.

By setting the degree of amplification of the amplifier 21, the measuring instrument 22 or other device can be caused to indicate the sludge level directly.

The meter can, however, also be used as a turbidity meter (turbidimeter) by placing or submerging the measurement head 3 into a suspension of known turbidity after which the amplification of the amplifier is to be adjusted. Then, the measuring head is placed in that suspension whose turbidity is to be measured and need not be constant. When using modern electronic equipment (not shown in detail) such turbidity measurement can be carried out down to full instrument reading at 1 FTU (Formazin Turbidity Unit = accepted standard turbidity unit).

The meter can also apparently be used to measure the distance to solid and floating objects without in any way coming into contact with them. The meter can be made very robust and is very suitable for use in difficult environments such as in dirty or corrosive liquids.

The meter shown as an example is very little subjected to fouling of or deposits on, or in-front-of, the windows 6 and 9. If required, these can be provided with a flushing device built into the measuring head in some suitable way so that a flushing fluid such as water or gas either intermittently or continuously flows along or against the outside of the windows. Flushing water can contain wetting agents, detergents, possibly even herbicides such as copper sulphate and the like which prevent the growth of algae and micro-organisms. A copper ring, a silver-coated ring or possibly a ring of another metal round the windows can be sufficient to prevent organic growth on the windows. The flushing water or gas can, depending on the operating conditions, be led off by the surrounding fluid or be sucked away.

For purposes of inspection and possible readjustment after a long period of operation it is not required to take up the meter from the fluid (here, water) in which the measurement is being made, nor to remove the fluid, if the measuring head includes an electrically controlled optical shunt between the light source 4 and the photo-cell 7, for example so that part of the light from the light source is reflected and passes through an electrically operated shutter to the photo-cell. The dimensioning and selected data can be such that, in the above-mentioned case, the same reading on the measuring instrument 22 is obtained as when a reference suspension or reflector with corresponding reflection factor is arranged at level 13.

Alternatively the meter can be arranged such that only the beam intersection area 17a above level 13 is used for measuring, provided that level 13 is made opaque (corresponding to the bottom 1) and that the distance and the said angle values are selected such that the photo-cell 7 does not receive any reflected light from the above level 12 even if the sludge layer level rises above level 12.

What I claim is:

1. An apparatus for measuring the level of turbidity in a fluid comprising:
    a fluidtight housing for placement in said fluid and having an optical window;
    a light source mounted in said housing for producing a beam of light which is directed via said window into said fluid and which diverges about an axis at an angle of between 3 and 10°;
    photosensitive means mounted in said housing separated from said light source and having a field of view into said fluid which diverges about an axis at an angle of between 3 and 10° and which intersects said divergent beam of light in said fluid, the area of intersection being symmetrically disposed about an axis extending away from said light source and the angle between the axes of said beam and field being no greater than 25° for measuring the light in said field scattered or reflected by particles causing said turbidity condition and producing an electrical turbidity signal which varies as a function of the cross-sectional area of said intersection at the level of said particles and, hence, the level of turbidity.

2. An apparatus as in claim 1, further including meter means connected to said photosensitive means for displaying the condition indicated by said electrical signal.

3. An apparatus as in claim 1 further including an optical screen extending outward from said window between said beam and said field of view for preventing direct inpingement of light from said source onto said photosensitive means.

4. An apparatus as in claim 1 including means for supplying an A.C. current to said source and said photosensitive means, and means connected to said source for modulating said A.C. signal at a frequency several times higher than the frequency of said A.C. signal and a filter connected to said photosensitive means having a lower limit frequency several times higher than the frequency of said A.C. signal but below the modulating frequency.

5. An apparatus as in claim 4, including an amplifier connected to said filter having a manually adjustable gain such that the output of said amplifier represents a zero level at a nominal zero for turbidity level.

6. An apparatus as in claim 1, wherein said light source is a luminous diode and said photosensitive means is a photocell.

* * * * *